United States Patent
Topolev

(10) Patent No.: US 7,658,707 B2
(45) Date of Patent: Feb. 9, 2010

(54) CLITORIS FRICTION STIMULATOR AND METHOD FOR STIMULATING EROGENIC ZONES OF A WOMAN DURING A COITION

(76) Inventor: Sergei E. Topolev, ul. Tokareva 8-181, Sestroretsk (RU) 197706

( * ) Notice: Subject to any disclaimer, the term of this patent is extended or adjusted under 35 U.S.C. 154(b) by 0 days.

(21) Appl. No.: 11/868,026

(22) Filed: Oct. 5, 2007

(65) Prior Publication Data

US 2008/0027275 A1  Jan. 31, 2008

Related U.S. Application Data

(63) Continuation of application No. PCT/RU2006/000121, filed on Mar. 16, 2006.

(30) Foreign Application Priority Data

Apr. 11, 2005  (RU) ............................... 2005110502

(51) Int. Cl.
*A61F 5/00* (2006.01)
(52) U.S. Cl. ....................................................... 600/38
(58) Field of Classification Search .............. 600/38–41
See application file for complete search history.

(56) References Cited

U.S. PATENT DOCUMENTS

| | | | | |
|---|---|---|---|---|
| 1,208,064 A | * | 12/1916 | Wilber | 601/138 |
| 1,334,716 A | * | 3/1920 | Shont | 15/222 |
| 3,912,266 A | * | 10/1975 | Gury | 482/125 |
| 4,969,894 A | * | 11/1990 | Hempstead-Harris | 606/234 |
| 5,383,841 A | | 1/1995 | Lilley | |
| 5,387,179 A | * | 2/1995 | Crivellaro | 600/38 |
| 5,713,830 A | * | 2/1998 | Tucker et al. | 600/38 |
| 5,736,213 A | * | 4/1998 | Meier | 428/76 |
| 2003/0083598 A1 | * | 5/2003 | Kobayashi et al. | 601/70 |

FOREIGN PATENT DOCUMENTS

| | | |
|---|---|---|
| RU | 2014059 C1 | 6/1994 |
| RU | 2080842 C1 | 6/1997 |
| SU | 443667 A | 4/1975 |
| WO | 98/42293 A1 | 10/1998 |

OTHER PUBLICATIONS

English translation of International Search Report from PCT/RU2006/000121, filed on Mar. 16, 2006.

* cited by examiner

*Primary Examiner*—Samuel G Gilbert
(74) *Attorney, Agent, or Firm*—Houston Eliseeva LLP

(57) ABSTRACT

The invention relates to medical engineering, in particular to exiting and attaining a woman orgasm. The invention consists of a stimulating element in the form of a strip having a relief surface, a connecting ring wearable on a coronal sulcus of a glans penis, a tension device and a method for stimulating erogenic zones of a woman during a coition. One end of the stimulating element is fixed to the coronal sulcus of a glans penis and the other end is connected to the tension device. During frictions, the stimulating element envelops a woman's pubic bone, reciprocatively moves and continuously touches the woman erogenic zones in the clitoris area, thereby exiting and additionally stimulating the clitoris. The aim of said invention is to amplify the sex sensation of a woman and to facilitate the orgasm.

14 Claims, 4 Drawing Sheets

CLITORIS FRICTION STIMULATOR AND METHOD FOR STIMULATING EROGENIC ZONES OF A WOMAN DURING A COITION

RELATED APPLICATIONS

This application is a Continuation application of PCT application serial number PCT/RU2005/000121 filed on Mar. 16, 2006, which in turn claims priority to Russian Application No. RU2005110502, filed on Apr. 11, 2005, both of which are incorporated herein by reference in their entirety.

BACKGROUND OF THE INVENTION

The invention relates to the medical technique, to the sexology domain, particularly to private use devices enhancing the excitement and facilitating the orgasm achievement by a woman, and could be used for correcting the sexual inadequacy.

The invention prior art is the RU Patent No. 2005446, Int. Cl$^5$ A61F 5/41 "Orgasmic ring", which disadvantage is in that it being fixed at the base of penis and having a small stimulating member being in a short-time contact with a clitoris only when fully invaginating a penis.

SUMMARY OF THE INVENTION

Essential features of the invention are: a stimulating member in the form of elastic band with a relief surface, which member providing a stimulation of erogenic zones of a woman; an adapting collar providing a fixation of the stimulating member on a penis in the region of coronal sulcus of penis; a tensioning device providing a reverse motion of the stimulating member; reciprocal motions of the stimulating member over pudendum, which motions providing a continuous stimulation of erogenic zones in the region of clitoris. The technical result consists in enhancing the sexual sensations of a woman and facilitating in the orgasm achievement.

The task of the invention consists in satisfying the man's and woman's sexual needs. When using the invention, women incapable to have the vaginal orgasm achieve the sexual discharge by the clitoris orgasm in a vaginal coition, which influences beneficially upon a harmonious sexual life of partners.

The invention consists of stimulating member in the form of a band with a relief surface, which band having an adapting collar at one end and a working section of tensioning device connected to the adapting collar at another end. The stimulating member is manufactured from elastic material meeting the design peculiarities of the product. The working section of the tensioning device is manufactured from the rubber or metal, and the mounting section is manufactured from a textile material of leather.

A method for stimulating erogenic zones of a woman during a coition consists in using motions of a penis and tensioning device for performing reciprocal movements of the stimulating member over pudendum with a constant contact in the clitoris region.

In general, according to one aspect, the invention features,

In general, according to another aspect, the invention features,

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

Figure 1:
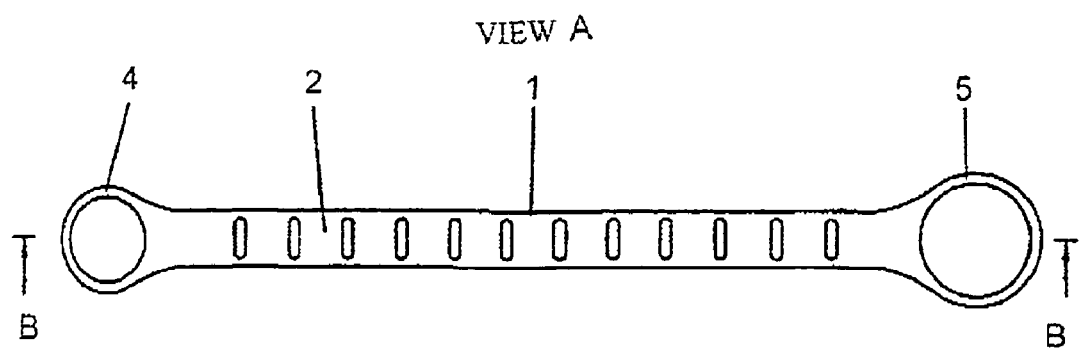
FIG. 1 shows an embodiment of the invention with the stimulating member having various relief pattern at working surfaces, and two adapting collars of different diameters, which embodiment being manufactured as a single piece, view A in FIG. 3.
Figure 2:
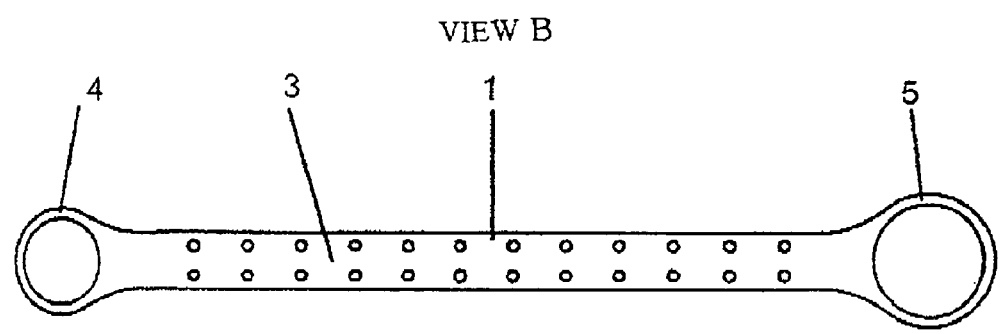
FIG. 2 shows the same, view Бin FIG. 3.
Figure 3:
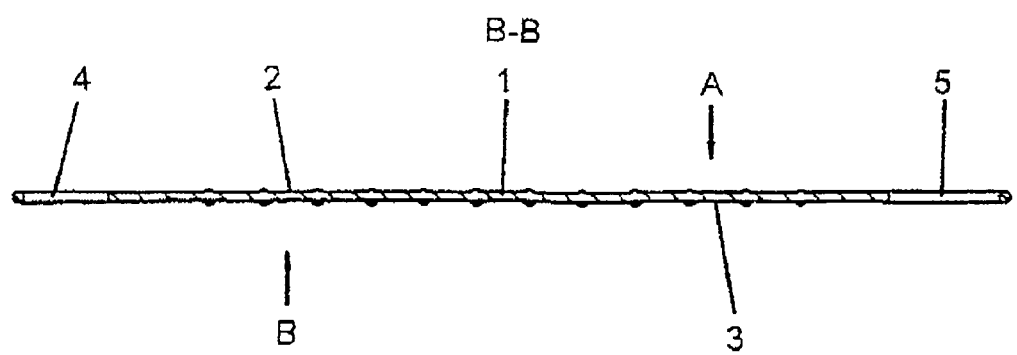
FIG. 3 shows the same, cross-section along the line B-B in FIG. 1.
Figure 4:
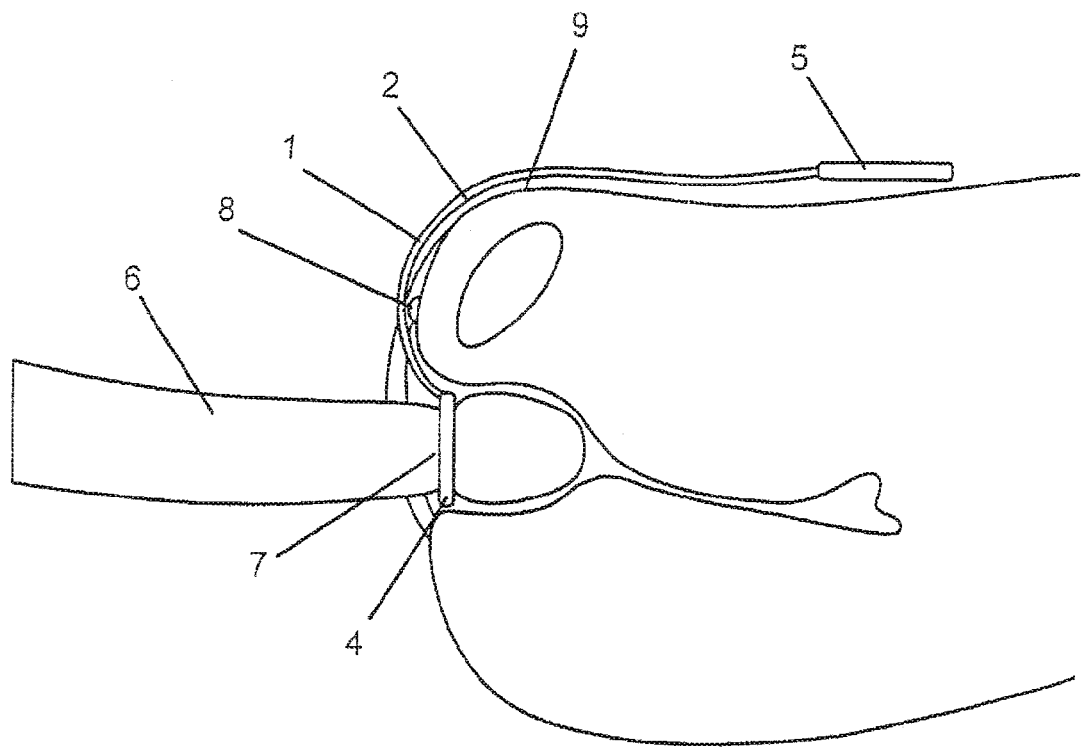
FIG. 4 shows the same, in the position of the initial stage of the penis motion (friction).
Figure 5:
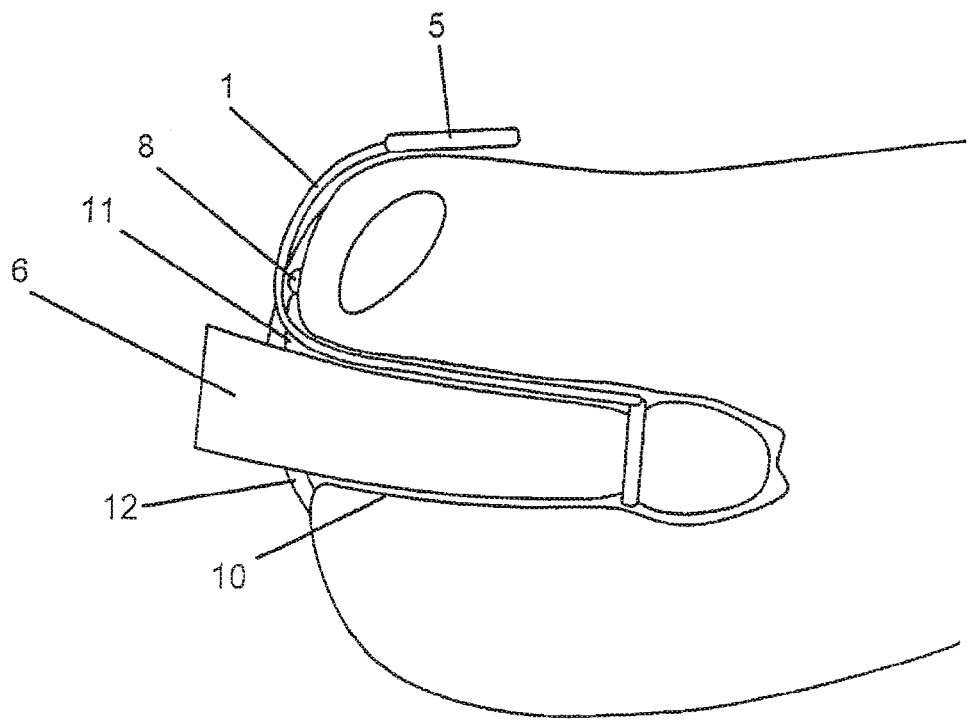
FIG. 5 shows the same, in the position of the final stage of the friction.

Embodiment of the invention in accordance with the variant shown in FIG. 1 is set forth below.

DETAILED DESCRIPTION OF THE PREFERRED EMBODIMENTS

Figure 6:
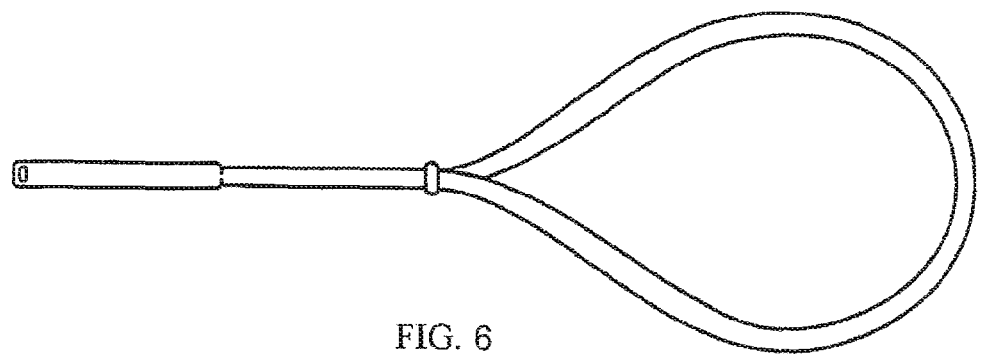
FIG. 6 shows the tension device.

The invention consists of a stimulating member 1 with relief surfaces 2 and 3 with different patterns for selecting the sensations, adapting collars 4 and 5 having different diameter for penis size matching. The adapting collar 4 is put on a penis 6 at the level of the coronal sulcus 7 with the selected side faced to the glans penis, and fixed by means of dense fitting. The free end of the stimulating member 1 with the adapting collar 5 is disposed near a woman's belly above the pubis 9 and joined with the tensioning device (not shown). When inputting the penis 6 into the vagina 10, the stimulating member 1 moves after the penis inward the pudendum, over the inner vulvar lips 11 between the outer vulvar lips 12 and stimulates the region of the clitoris 8 due to adjoining the outer genitalia. When moving the penis 6 back, the tensioning device pulls the stimulating member 1 at the adapting collar 5 backward, which stimulates the woman's clitoris 8 as well. The tensioning device (FIG. 6) consists of a working section with a hole for fastening the stimulating member, joined with the mounting section in the form of belt with adjustable loop size, which belt being put on the woman's neck, breast or waist.

Figure 7:
FIG. 7 shows the adapting collar with the changing diameter.
Figure 8:
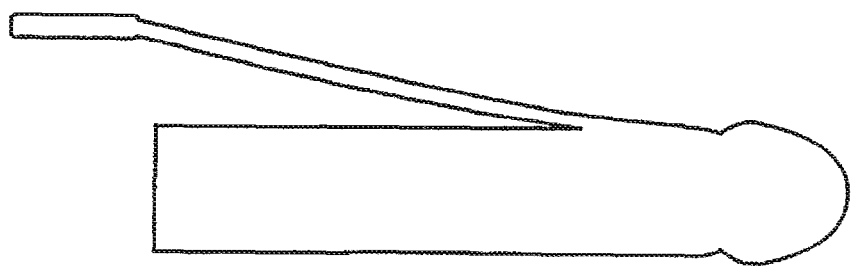
FIG. 8 shows the longitudinal section of the embodiment with the junction of the stimulating member and phalloprosthesis.
Figure 9:
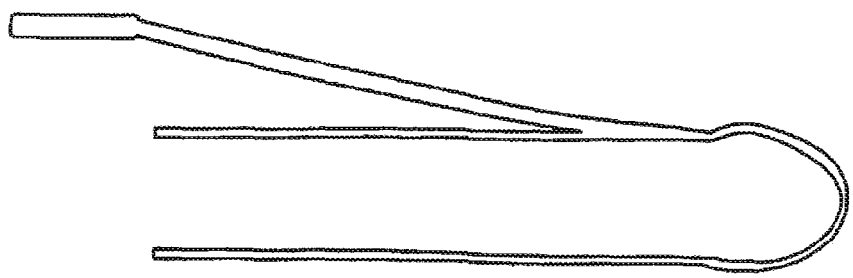
FIG. 9 shows the longitudinal section of the embodiment with the junction of the stimulating member and condom.
Figure 10:
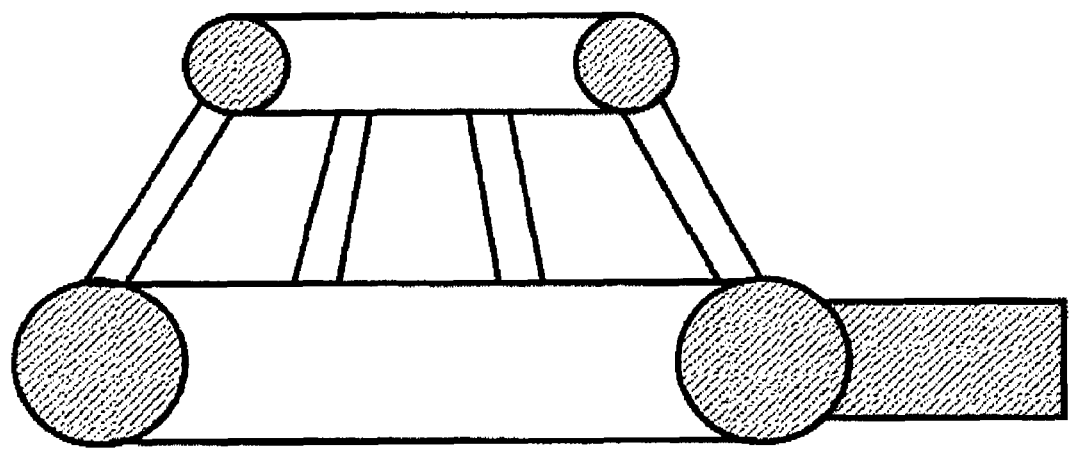
FIG. 10 shows an auxiliary collar of a smaller diameter than the adapting collar coupled by jumper straps with the adapting collar.

Another embodiment consists in manufacturing separately the adapting collar and stimulating member with the possibility for adjoining thereof. One more embodiment of the invention is the adapting collar of a special form for fixing on a penis in the form of a main collar coupled by jumper straps with the auxiliary collar of the smaller diameter. Yet one more embodiment of the invention is the adapting collar having the ellipsoidal section with the wide side directed inwards and having a skid resistant relief for fixing on the penis. Yet one more embodiment of the invention is the stimulating member with the adapting collar having the variable diameter (FIG. 7) and one free elongated end, and a locking device permit-ting to fix the free end of the collar within the member with a certain step. Yet one more embodiment of the invention is the stimulating member that could be made as a single device with a phalloprosthesis or vibrator (FIG. 8), or be adjoined therewith by means of any methods. Yet one more embodiment of the invention is the stimulating member that could be made as a single device with a condom (FIG. 9).

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for a penis for stimulating erogenous zones of woman's genitalia, comprising:
   a flexible stimulating member having a relief surface and a width sufficient for stimulating a zone of pudendum in the region of clitoris, the stimulating member having a length sufficient for and capable of being inserted into a vagina together with a penis and covering a woman's pubis;
   the stimulating member
      comprising at one of its ends an adapting collar for putting on a coronal sulcus of the penis and for fixing the end on the penis for providing a motion of the stimulating member over a pudendum when moving the penis within the vagina and
      comprising at its other end a graspable portion or a means for attaching a tensioning device;
      the device further comprising an auxiliary collar of the smaller diameter than the adapting collar, the auxiliary collar being coupled circumferentially with the adapting collar by jumper straps for disposing the auxiliary collar on the top of the glans penis and ensuring additional fixation of the end of the stimulating member on the penis.

2. The device in accordance with claim 1, wherein the adapting collar has a capability for varying the circumference size.

3. The device in accordance with claim 2, wherein the stimulating member is made in the form of elastic band.

4. The device in accordance with claim 1, wherein the stimulating member is made in the form of elastic band.

5. The device in accordance with claim 1, wherein the adapting collar has an ellipsoid cross-section with the wide side directed inwards.

6. A device for stimulating erogenous zones of woman's genitalia, comprising:
   a flexible stimulating member having a relief surface and a width sufficient for stimulating a zone of pudendum in the region of clitoris,
   a phallic prosthesis, vaginal vibrator, or condom,
   the stimulating member having a length sufficient for and capable of being inserted into a vagina together with the phallic prosthesis, vaginal vibrator, or a penis in the condom and covering a woman's pubis,
   the stimulating member either being configured for coupling by one of ends thereof with a distal end of the phallic prosthesis or vaginal vibrator, or joined by one of ends thereof with a distal end of the phallic prosthesis, vaginal vibrator, or condom, thereby forming in conjunction with it a single device for providing a motion of the stimulating member over a pudendum when moving the phallic prosthesis, vaginal vibrator or condom within the vagina and comprising at its other end a graspable portion or a means for attaching a tensioning device.

7. The device in accordance with claim 6, wherein the stimulating member is made in the form of elastic band.

8. A device for stimulating erogenous zones of woman's genitalia, comprising:
   a flexible stimulating member having a relief surface and a width sufficient for stimulating a zone of pudendum in the region of clitoris, the stimulating member having a length sufficient for inputting fully into a vagina and covering a woman's pubis,
   a tensioning device coupled with the stimulating member and having a working section providing a reverse motion of the stimulating member, and a fixed section joined therewith,
   the stimulating member comprising at one of its ends an adapting collar for putting on a coronal sulcus of a penis and fixing the end on the penis for providing a motion of the stimulating member over a pudendum when moving the penis within the vagina.

9. The device in accordance with claim 8, wherein the adapting collar has a skid-resistant relief for fixing on the penis.

10. A device for stimulating erogenous zones of woman's genitalia, comprising:
    a flexible stimulating member having a relief surface and a width sufficient for stimulating a zone of pudendum in the region of clitoris,
    a phallic prosthesis, vaginal vibrator or condom,
    a tensioning device coupled with the stimulating member and having a working section providing a reverse motion of the stimulating member, and a fixed section joined therewith,
    the stimulating member having a length sufficient for inputting fully into a vagina and covering a woman's pubis,
    the stimulating member either being configured for coupling by one of ends thereof with a distal end of the phallic prosthesis or vaginal vibrator, or joined by one of ends thereof with a distal end of the phallic prosthesis, vaginal vibrator or condom, thereby forming in conjunction with it a single device for providing a motion of the stimulating member over a pudendum when moving the phallic prosthesis, vaginal vibrator or condom within the vagina.

11. A method for stimulating erogenous zones of a woman during a coition comprising a step of moving reciprocally over pudendum a flexible stimulating member having a width sufficient for stimulating a zone of pudendum in the region of clitoris, the flexible stimulating member having a length sufficient for and capable of being inserted into a vagina together with a penis, phallic prosthesis, vaginal vibrator or a penis in a condom and covering a woman's pubis, and being coupled by one end with a penis coronal sulcus, a distal end of a phallic prosthesis, a distal end of a vaginal vibrator, or a distal end of a condom, and by another end with a tensioning device for providing a reciprocal motion of the stimulating member as a result of moving the penis, phallic prosthesis, vaginal vibrator or condom within the vagina.

12. A device for stimulating erogenous zones of woman's genitalia, comprising:

a flexible stimulating member having a relief surface and a width sufficient for stimulating a zone of pudendum in the region of clitoris, the stimulating member having a length sufficient for inputting fully into a vagina and covering a woman's pubis, a tensioning device coupled with the stimulating member and having a working section providing a reverse motion of the stimulating member, and a fixed section joined therewith, the stimulating member comprising at one of its ends an adapting collar for putting on a coronal sulcus of a penis and fixing the end on the penis for providing a motion of the stimulating member over a pudendum when moving the penis within the vagina, the adapting collar having an ellipsoid cross-section with the wide side directed inwards.

13. A device for stimulating erogenous zones of woman's genitalia, comprising:

a flexible stimulating member having a relief surface and a width sufficient for stimulating a zone of pudendum in the region of clitoris, the stimulating member having a length sufficient for inputting fully into a vagina and covering a woman's pubis, a tensioning device coupled with the stimulating member and having a working section providing a reverse motion of the stimulating member, and a fixed section joined therewith, the stimulating member comprising at one of its ends an adapting collar for putting on a coronal sulcus of a penis and fixing the end on the penis for providing a motion of the stimulating member over a pudendum when moving the penis within the vagina, an auxiliary collar of the smaller diameter than the adapting collar, the auxiliary collar being coupled circumferentially with the adapting collar by jumper straps for disposing the auxiliary collar on the top of the glans penis and ensuring additional fixation of the end of the stimulating member on the penis.

14. A device for stimulating erogenous zones of woman's genitalia, comprising:

a flexible stimulating member having a relief surface and a width sufficient for stimulating a zone of pudendum in the region of clitoris, the stimulating member having a length sufficient for inputting fully into a vagina and covering a woman's pubis, a tensioning device coupled with the stimulating member and having a working section providing a reverse motion of the stimulating member, and a fixed section joined therewith, the stimulating member comprising at one of its ends an adapting collar for putting on a coronal sulcus of a penis and fixing said end on the penis for providing a motion of the stimulating member over a pudendum when moving the penis within the vagina, wherein the adapting collar has a capability for varying the circumference size.

* * * * *